(12) United States Patent
Krochmal et al.

(10) Patent No.: US 6,750,341 B2
(45) Date of Patent: Jun. 15, 2004

(54) PREPARATION OF RISPERIDONE

(75) Inventors: Barnaba Krochmal, Jerusalem (IL); Dov Diller, Jerusalem (IL); Ben-Zion Dolitzky, Petach Tiqva (IL); Judith Aronhime, Rehovot (IL)

(73) Assignee: Teva Pharmaceutical Industries Ltd., Petah Tiqva (IL)

(*) Notice: Subject to any disclaimer, the term of this patent is extended or adjusted under 35 U.S.C. 154(b) by 0 days.

(21) Appl. No.: 09/929,808

(22) Filed: Aug. 14, 2001

(65) Prior Publication Data

US 2002/0115673 A1 Aug. 22, 2002

Related U.S. Application Data

(60) Provisional application No. 60/225,361, filed on Aug. 14, 2000, and provisional application No. 60/243,263, filed on Oct. 25, 2000.

(51) Int. Cl.[7] ............................................. C07D 239/70
(52) U.S. Cl. ...................................................... 544/282
(58) Field of Search .......................................... 544/282

(56) References Cited

U.S. PATENT DOCUMENTS

| 4,804,663 | A |   | 2/1989 | Kennis et al. | ............... 514/258 |
| 5,158,952 | A | * | 10/1992 | Janssen et al. | ............... 514/258 |
| 2002/0115672 | A1 | * | 8/2002 | Krochmal et al. | ..... 514/259.41 |
| 2002/0193386 | A1 |   | 12/2002 | Pfeiffer et al. | ......... 514/259.41 |

OTHER PUBLICATIONS

John Haleblian et al "Pharmaceutical Applications of Polymorphism"; Journal of Pharmaceutical Sciences, vol. 58, No. 8, Aug. 1969—pp. 911–929.

John K. Haleblian "Characterization of Habits and Crystalline Modification of Solids and Their Pharmaceutical Applications"; Journal of Pharmaceutical Sciences, vol. 64, No. 8, Aug. 1975—PP1269–1288.

G. Michael Wall "Pharmaceutical Applications of Drug Crystal Studies", Pharmaceutical Manufacturing, vol. 3, No. 2, Feb. 1986; PP 33–42.

O.M. Peeters et al., Structure of 3—{2–[4–(6–Fluoro–1, 2–benzisoxazole–3–yl)piperidino]ethyl}—6,7,8, 9–tetrahydro–2–methyl–4–H–pyrido–[-2–α] pyrimidin–4–one (Risperidone), Acta Crystallographica (1993), Section C49, 1698–1700.

* cited by examiner

Primary Examiner—Brenda Coleman
(74) Attorney, Agent, or Firm—Kenyon & Kenyon

(57) ABSTRACT

The present invention is directed to the novel forms of risperidone, designated Form A, Form B and Form E. Methods for their preparation are also disclosed. The present invention also relates to processes for making risperidone. Pharmaceutical compositions containing the new forms of risperidone and methods of using them are also disclosed.

19 Claims, 3 Drawing Sheets

PREPARATION OF RISPERIDONE

CROSS REFERENCE TO RELATED APPLICATIONS

This application claims the benefit of provisional application Ser. No. 60/225,361, filed Aug. 14, 2000; and provisional application Ser. No. 60/243,263, filed Oct. 25, 2000. Both of these applications are incorporated herein by reference.

FIELD OF THE INVENTION

The present invention relates to novel polymorphic forms of risperidone. The present invention also relates to methods of making polymorphic forms of risperidone.

BACKGROUND OF THE INVENTION

RISPERDAL® (risperidone) is an antipsychotic agent belonging to a new chemical class, the benzisoxazole derivatives. The chemical designation is 3-[2-[4-(6-fluoro-1,2-benzisoxazol-3-yl)-1-piperidinyl]ethyl]-6,7,8,9-tetrahydro-2-methyl-4H-pyrido[1,2-a]pyrimidin-4-one.

U.S. Pat. No. 4,804,663, the contents of which are incorporated by reference, describes a synthesis of risperidone. Risperidone may be prepared by condensation of the following two intermediates, 6-fluoro-3-(4-piperidinyl)-1,2-benzisoxazole (Compound I) and 3-(2-chloroethyl)-6,7,8,9-tetrahydro-2-methyl-4H-pyrido[1,2-a]pyrimidin-4-one (Compound II) in dimethylformamide (DMF) in basic conditions ($Na_2CO_3$ or $K_2CO_3$) with catalytic amount of potassium iodide (KI). The crude risperidone product (III) is crystallized from a mixture of DMF and isopropanol with an overall yield of 46%.

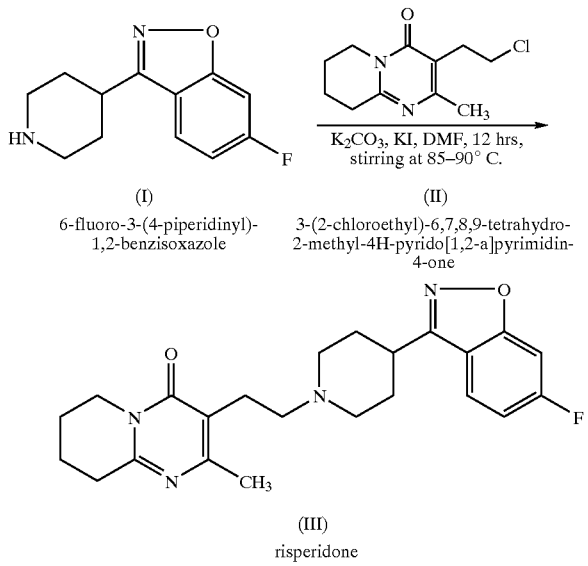

(I)
6-fluoro-3-(4-piperidinyl)-1,2-benzisoxazole (II)
3-(2-chloroethyl)-6,7,8,9-tetrahydro-2-methyl-4H-pyrido[1,2-a]pyrimidin-4-one $K_2CO_3$, KI, DMF, 12 hrs, stirring at 85–90° C.

(III)
risperidone

Polymorphism is the occurrence of different crystalline forms of a single compound and it is a property of some compounds and complexes. Thus, polymorphs are distinct solids sharing the same molecular formula, yet each polymorph may have distinct physical properties. Therefore, a single compound may give rise to a variety of polymorphic forms where each form has different and distinct physical properties, such as different solubility profiles, different melting point temperatures and/or different x-ray diffraction peaks. Since the solubility of each polymorph may vary, identifying the existence of pharmaceutical polymorphs is essential for providing pharmaceuticals with predicable solubility profiles. It is desirable to investigate all solid state forms of a drug, including all polymorphic forms, and to determine the stability, dissolution and flow properties of each polymorphic form. Polymorphic forms of a compound can be distinguished in a laboratory by X-ray diffraction spectroscopy and by other methods such as, infrared spectrometry. For a general review of polymorphs and the pharmaceutical applications of polymorphs see G. M. Wall, *Pharm Manuf.* 3, 33 (1986); J. K. Haleblian and W. McCrone, *J. Pharm. Sci.*, 58, 911 (1969); and J. K. Haleblian, *J. Pharm. Sci.*, 64, 1269 (1975), all of which are incorporated herein by reference.

SUMMARY OF THE INVENTION

An object of the processes of the present invention is to provide more efficient and quicker methods for making pure risperidone. We have now found that the synthesis of risperidone from compounds I and II can done in acetonitrile and isopropanol, without using DMF, to give an improved and higher yield of about 75%.

The present invention provides a process for the preparation of risperidone from the following two intermediates, 6-fluoro-3-(4-piperidinyl)-1,2-benzisoxazole (Compound I) and 3-(2-chloroethyl)-6,7,8,9-tetrahydro-2-methyl-4H-pyrido[1,2-a]pyrimidin-4-one (Compound II) in acetonitrile.

It has also been found that the crude risperidone can be efficiently crystallized in high yield from an alcohol, for example, isopropanol, butanol, ethanol, or methanol; or from a ketone, for example, acetone or ethyl methyl ketone, without the need of using DMF, which is harmful to humans and is a very difficult solvent to remove.

Polymorphs of risperidone are mentioned in the Summary Basis of Approval (SBA) of New Drug Application 20-272 and 20-588, however the SBA does not identify them by recognized methods of crystal structure identification such as x-ray diffraction.

The present invention also provides forms of risperidone designated risperidone Form A, Form B and Form E.

The present invention further provides a process for making risperidone comprising reacting Compound I with Compound II to form crude risperidone (III) in a solvent selected from the group consisting of acetonitrile, isopropanol, methyl ethyl ketone and iso-butanol.

In another embodiment, the crude risperidone is recrystallized from an alcohol; a mixture of alcohols; a mixture of water and alcohol; or from a ketone, e.g., acetone. In another embodiment, the alcohol is selected from the group consisting of methanol, ethanol, isopropanol, propanol, butanol, sec-butanol, iso-butanol and t-butanol. In another embodiment, the alcohol is isopropanol. In another embodiment, the alcohol is acetonitrile. In another embodiment, the alcohol is isopropanol. In another embodiment, the alcohol is iso-butanol. In another embodiment, the ketone is acetone. In another embodiment, the acetone is methyl ethyl ketone.

The present invention also provides risperidone Form A which is characterized by x-ray powder diffraction peaks at 14.2±0.2, 21.3±0.2 degrees two-theta. The present invention also provides risperidone Form A of further characterized by x-ray powder diffraction peaks at 10.6±0.2, 11.4±0.2, 16.4±0.2, 18.9±0.2, 19.9±0.2, 22.5±0.2, 23.3±0.2, 25.4±0.2, 27.6±0.2, 29.0±0.2 degrees two-theta.

The present invention also provides a risperidone polymorph that is characterized by a powder x-ray diffraction pattern substantially as depicted in FIG. 1.

The present invention also provides risperidone Form B which is characterized by x-ray powder diffraction peaks at 14.0±0.2 and 21.7±0.2 degrees two-theta.

The present invention also provides a risperidone polymorph that is characterized by a powder x-ray diffraction pattern substantially as depicted in FIG. 2.

The present invention also provides risperidone Form B which is further characterized by x-ray powder diffraction peaks at 10.8±0.2, 11.9±0.2, 12.6±0.2, 14.0±0.2, 17.5±0.2, 18.3±0.2, 19.9±0.2, 21.0±0.2, 21.7±0.2 degrees two-theta.

The present invention also provides risperidone Form E which is characterized by x-ray powder diffraction peaks at 16.5±0.2, 21.7±0.2 degrees two-theta.

The present invention also provides risperidone Form E which is further characterized by x-ray powder diffraction peaks at 16.5±0.2, 12.6±0.2, 21.7±0.2, 15.6±0.2, 17.0±0.2, 18.4±0.2, 19.1±0.2, 21.3±0.2, 24.0±0.2, 24.9±0.2, 27.0±0.2 degrees two-theta.

The present invention also provides a risperidone polymorph that is characterized by a powder x-ray diffraction pattern substantially as depicted in FIG. 3.

The present invention also provides a process for preparing risperidone Form B comprising the steps of: dissolving risperidone in a substantially water soluble alcohol having 1 to 4 carbon atoms where the ratio of risperidone to alcohol is about 1:7.5 to about 1:9; adding water to facilitate precipitation; and isolating risperidone Form B.

The present invention also provides a process for preparing risperidone Form B comprising the steps of: dissolving risperidone in chloroform; adding cyclohexane or hexane to facilitate precipitation; and isolating risperidone Form B.

The present invention also provides a process for preparing risperidone Form B comprising the steps of: dissolving risperidone in an aqueous solution of HCl; adding an aqueous solution of $Na_2CO_3$; and isolating risperidone Form B.

The present invention also provides a process for preparing risperidone Form A comprising the steps of: dissolving risperidone in an organic solvent selected from the group consisting of dimethylformamide, tetrahydrofuran, acetone, benzene, ethyl methyl ketone, n-butanol, methanol, isopropanol, absolute ethanol, acetonitrile, toluene, dimethyl sulfoxide, iso-butanol, and ethyl acetate or mixtures thereof; heating the solvent to reflux; cooling the solvent to facilitate precipitation; and isolating risperidone Form A.

The present invention also provides a process for preparing risperidone Form A comprising the steps of: dissolving risperidone in dichloromethane; adding cyclohexane or hexane to facilitate precipitation; and isolating risperidone Form A.

The present invention also provides a method for preparing risperidone Form A comprising the step of: heating risperidone Form B at a temperature of about 25° C. to about 80° C. for a time sufficient to induce to formation of risperidone Form A; and isolating risperidone Form A. In another embodiment, the heating takes place under reduced pressure or at atmospheric pressure. In another embodiment, the temperature is about 80° C. In another embodiment, the time for heating is about 16 to about 20 hours.

The present invention also provides a process for preparing risperidone Form E comprising the steps of: dissolving risperidone in isopropanol where the ratio of risperidone to isopropanol is about 1:12; adding water to facilitate precipitation; and isolating risperidone Form E.

DETAILED DESCRIPTION OF THE INVENTION

Synthesis of Risperidone

Figure 1:
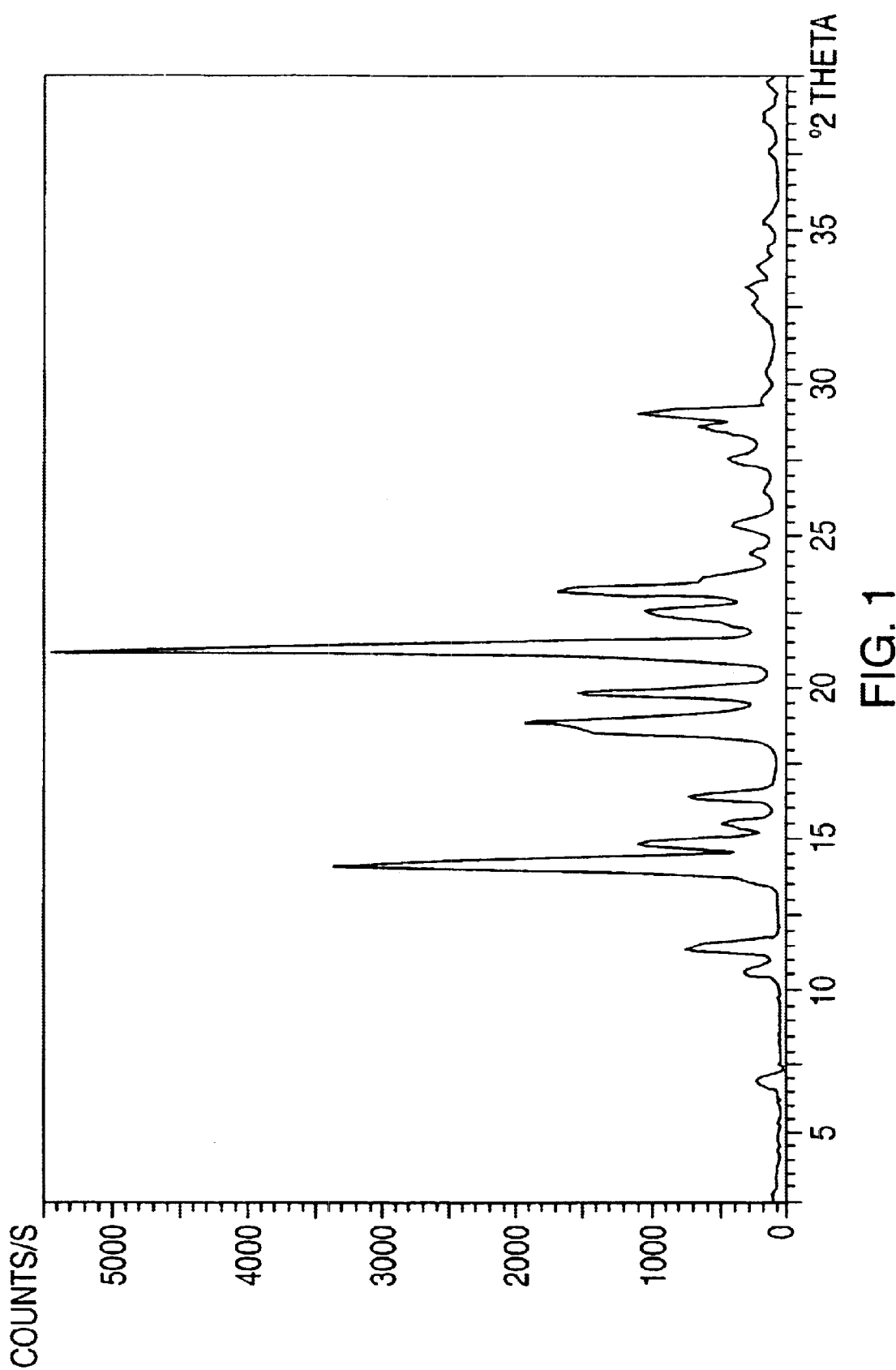
FIG. 1 is a characteristic x-ray powder diffraction spectrum of risperidone Form A.

The present invention provides new processes for preparing risperidone from the following two intermediates, 6-fluoro-3-(4-piperidinyl)-1,2-benzisoxazole (I) and 3-(2-chloroethyl)-6,7,8,9-tetrahydro-2-methyl-4H-pyrido[1,2-a]pyrimidin-4-one (II) using acetonitrile, isopropanol, iso-butanol, or methyl ethyl ketone as the solvent, which eliminates the need to use DMF as a solvent. By the methods of the present invention, risperidone is prepared by adding, 3-(2-chloroethyl)-6,7,8,9-tetrahydro-2-methyl-4H1-pyrido[1,2-a]pyrimidin-4-one (Compound II or "the chlorine derivative"); 6-fluoro-3-(4-piperidinyl)-1,2-benzisoxazole (Compound I or "the piperidine derivative"); sodium carbonate; and potassium iodide (66 mg) into a flask containing the solvent isopropanol, acetonitrile, methyl ethyl ketone or iso-butanol. Preferably, the Compound I and Compound II are present in a ratio of about 1:1. The reaction mixture is then heated by methods known in the art, such as, by placing the flask in an oil bath which is heated from about 60° C. to about 85° C., and the reaction is allowed to reflux for a time sufficient to complete the formation of risperidone, about 9 hours to overnight. Preferably, the reaction mixture is heated to about 60° C. to about 67° C. Preferably the reaction is heated for about 9 hours when the solvent is isopropanol. Preferably the reaction mixture is heated overnight when the solvent is methyl ethyl ketone or iso-butanol. Preferably the reaction is heated for about 17 hours when the solvent is acetonitrile. Upon completion of the reaction, the mixture is cooled by methods known in the art to induce the precipitation of risperidone.

The resulting precipitated risperidone is filtered and the filter cake is washed in the filter with a small amount of isopropanol, acetone or a mixture of acetone and water. The filter cake is then slurried, filtered and easily dried by conventional methods to give crude risperidone in a yield of about 63 to 74% yield. The present method eliminates the difficult step of removing DMF from the crude risperidone.

The present invention also relates to new processes for recrystallizing crude risperidone from; an alcohol, such as, methanol, ethanol, isopropanol, propanol, butanol, sec-butanol and t-butanol; a mixture of alcohols containing any combination of, methanol, ethanol, isopropanol, propanol, butanol, sec-butanol and t-butanol; or a mixture of water and alcohol where the alcohol is one or more of the following alcohols, methanol, ethanol, isopropanol, propanol, butanol, sec-butanol and t-butanol. The present recrystallization eliminates the use of the difficult to remove and potentially harmful solvent DMF. Preferably, the solvent is isopropanol. By the methods of the present invention, crude risperidone is recrystallized by dissolving the crude risperidone in a solvent which is hot. Preferably, the solvent is heated to reflux. Preferably the crude risperidone and solvent are present in a ratio of about 10 to about 15, more preferably the ratio is about 11 to 13, most preferably the ratio is about 11.5 to about 12.5. Preferably the solvent is isopropanol. The hot mixture is then filtered hot and allowed to cool where upon purified risperidone precipitates. The mixture is filtered by conventional methods to give high purity risperidone with a purity of about 99.7 to about 99.8%. The overall yield of the present method of synthesis and recrystallization of risperidone is about 60 to about 63%.

The present invention also provides new processes for recrystallizing crude risperidone from a solvent that is a ketone, such as, acetone. The present recrystallization eliminates the use of the difficult to remove and potentially harmful solvent DMF. Preferably, the solvent is acetone. By the methods of the present invention, crude risperidone is recrystallized by dissolving the crude risperidone in a ketone, which is hot. Preferably, the ketone is heated to reflux. Preferably the crude risperidone and solvent are present in a ratio of about 25 to about 40, more preferably the ratio is about 28 to about 32. Preferably the solvent is acetone. The hot mixture is then filtered hot and allowed to cool where upon purified risperidone precipitates. The mixture is filtered by conventional methods to give high purity risperidone with a purity of about 99.7 to about 99.8%. The overall yield of the present method of synthesis and recrystallization of risperidone is about 60 to about 63%.

Risperidone Form A

The present invention also relates to a novel risperidone crystalline form designated Form A and processes for making risperidone Form A. Risperidone Form A is characterized by unique strong powder x-ray diffraction peaks at $14.2\pm0.2$, and $21.3\pm0.2$ degrees two-theta and medium intensity peaks at $10.6\pm0.2$, $11.410.2$, $16.4\pm0.2$, $18.9\pm0.2$, $19.9\pm0.2$, $22.5\pm0.2$, $23.3\pm0.2$, $27.6\pm0.2$, $25.4\pm0.2$, and $29.0\pm0.2$ degrees two-theta.

Another aspect of this invention is a method of preparing risperidone Form A. In the method of preparing risperidone Form A, risperidone Form A is crystallized from risperidone at the reflux temperature of an organic solvent, such as, DMF, tetrahydrofuran (THF), acetone, benzene, ethyl methyl ketone, n-butanol, methanol, isopropanol, absolute ethanol, acetonitrile, toluene, dimethyl sulfoxide (DMSO), iso-butanol or ethyl acetate. By the methods of the present invention, risperidone is added to in a minimum amount of organic solvent by heating the mixture to facilitate dissolution of the risperidone. Upon complete dissolution of the risperidone, the solution is left to cool to room temperature to induce the precipitation of risperidone Form A. After the solution has reached room temperature, it is further cooled in an ice bath and then filtered to isolate risperidone Form A. Suitable volumes of solvent required for the present methods are listed below in Example 11 and in Table 1.

Another aspect of this invention is a method of preparing risperidone Form A; or a mixture of risperidone Form A and other forms of risperidone, including risperidone Form B, by dissolving risperidone in dichloromethane and adding cyclohexane or hexane to induce precipitation. By the methods of the present invention, risperidone is dissolved in dichloromethane in a ratio of about 1 to about 9. Hexane or cyclohexane is then added until a cloudy dispersion is formed. The risperidone Form A is then isolated by filtration.

Another aspect of this invention is a method of preparing risperidone Form A by heating risperidone Form B. By the methods of the present invention, risperidone Form A is prepared by heating risperidone Form B, or a mixture of risperidone Form A and B at temperatures above room temperature, preferably at about 80° C., under either reduced pressure or at atmospheric pressure, for a period of several minutes to several hours, preferably 16–20 hours. One embodiment of the present method for preparing risperidone Form A is heating risperidone Form B, or a mixture of risperidone Form B and risperidone Form A, at 80° C. overnight, under reduced pressure or at atmospheric pressure, and isolating the resulting crystals of risperidone Form A. An alternative method of preparing risperidone Form A by heating risperidone Form B includes, heating risperidone Form B in a differential scanning calorimeter, at the rate of 5 to 20 degrees per minute, to yield risperidone Form A.

Risperidone Form B

The present invention also relates to a novel crystalline form of risperidone, denominated risperidone Form B. Risperidone Form B is characterized by unique strong powder x-ray diffraction peaks at $14.0\pm0.2$ and $21.7\pm0.2$ degrees two-theta, and medium peaks at $10.8\pm0.2$, $11.9\pm0.2$, $12.6\pm0.2$, $17.5\pm0.2$, $18.3\pm0.2$, $19.9\pm0.2$, $21.0\pm0.2$, $21.3\pm0.2$ degrees two-theta, and is well distinguished from risperidone Form A. The presence of risperidone Form B in a mixture with risperidone Form A is detected by the appearance mainly of the strongest peaks at $21.7\pm0.2$, $17.5\pm0.2$, $18.4\pm0.2$, and also by the other peaks which appear at $11.9\pm0.2$, $12.6\pm0.2$ degrees two theta.

The DSC thermogram of risperidone Form B is characterized by a solid—solid transition to risperidone Form A detected in a small endotherm at 164° C. followed by a small exotherm and a melting endotherm of risperidone Form A at 171° C.

Another aspect of this invention is a method of preparing risperidone Form B by dissolving risperidone in an alcohol having 1 to 4 carbon atoms, followed by the addition of water to facilitate the precipitation of risperidone Form B. Preferably the ratio of risperidone to alcohol is about 1:7.5 to about 1:9. Preferably the alcohol is ethanol or methanol.

Another aspect of this invention is a method of preparing risperidone Form B pure or in a mixture with another form of risperidone, such as, risperidone Form A, which includes dissolving risperidone in a hot solution of aqueous HCl followed by the addition of aqueous $Na_2CO_3$ to induce precipitation of risperidone Form B. By the methods of the present invention, risperidone is added to 0.5 N HCl in a ratio of about 1:6. Water is added in an amount equal to about two thirds the volume of HCl used. The solution is heated to induce dissolution of the risperidone. Sodium carbonate is then added until a pH of about 8 is reached, to facilitate precipitation. The solution is cooled and risperidone Form B is isolated by filtration.

Another aspect of this invention is a method of preparing risperidone Form B pure or in a mixture with another form of risperidone such as risperidone Form A, wherein risperidone is dissolved in chloroform followed by the addition of cyclohexane or hexane to facilitate precipitation. By the methods of the present invention, risperidone is dissolved in chloroform in a ratio of about 1:6 followed by the addition of hexane of cyclohexane in an amount sufficient to produce a cloudy dispersion. The risperidone Form B is then isolated upon filtration.

Risperidone Form E

The present invention also relates to a novel crystalline form of risperidone, denominated risperidone Form E. Risperidone Form E is characterized by typical strong x-ray peaks at $16.5\pm0.2$, $21.7\pm0.2$ degrees two-theta, and medium x-ray peaks at $12.6\pm0.2$, $15.6\pm0.2$, $17.0\pm0.2$, $18.4\pm0.2$, $19.1\pm0.2$, $21.3\pm0.2$, $24.0\pm0.2$, $24.9\pm0.2$, $27.0\pm0.2$ degrees two-theta Another aspect of this invention is a method of preparing risperidone Form E. By the methods of the present invention, risperidone is dissolved in isopropanol in a ratio of about 1 to 12. Water is then added until a cloudy dispersion is formed thereby facilitating the precipitation of risperidone Form E. Risperidone Form E is isolated upon filtration of the dispersion.

In accordance with the present invention, these new forms of risperidone may be prepared as pharmaceutical compositions that are particularly useful for the management of the manifestations of psychotic disorders. Such compositions comprise one of the new forms of risperidone with pharmaceutically acceptable carriers and/or excipients known to one of skill in the art.

Preferably, these compositions are prepared as medicaments to be administered orally, or intravenously. Suitable forms for oral administration include tablets, compressed or coated pills, dragees, sachets, hard or gelatin capsules, sub-lingual tablets, syrups and suspensions. While one of ordinary skill in the art will understand that dosages will vary according to the indication, age of the patient, etc., generally polymorphic forms of risperidone of the present invention will be administered at a daily dosage of about 4 to about 16 mg per day, and preferably about 4 to about 8 mg per day.

EXAMPLES

The present invention will now be further explained in the following examples. However, the present invention should not be construed as limited thereby.

Methods

Conditions for obtaining Powder X-ray Diffraction (PXRD) patterns: The powder X-ray diffraction patterns were obtained by methods known in the art using a Philips X-ray powder diffractometer, Phillips Generator TW 1830; Goniometer PW3020; MPD Control PW3710; X-Ray tube with Cu target anode; Monochromator proportional counter; Divergence slits 1°, Receiving slit 0.2 mm, Scatter slit 1°; 40 KV, 30 mA; and Scanning speed step 0.05 degrees to 2 degrees/min.

The differential scanning calorimeter thermograms were obtained by methods known in the art using a DSC Mettler 821 Star$^e$. The weight of the samples was about 3–5 mg. The temperature range of scans was 30° C.–250° C. at a rate of 10C/min. Samples were purged with nitrogen gas at a flow rate of 40 mL/min. Standard 40 μl aluminum crucibles were used having lids with three small holes.

Example 1

Synthesis of Risperidone

Isopropanol (20 mL), 3-(2-chloroethyl)-6,7,8,9-tetrahydro-2-methyl-4H-pyrido[1,2-a]pyrimidin-4-one (Compound II)("the chlorine derivative")(2.63 g, 10 mmoles, 1 eq.), 6-fluoro-3-(4-piperidinyl)-1,2-benzisoxazole (Compound I)("the piperidine derivative") (2.17 g, 10 mmoles, 1 eq.), sodium carbonate (3.18 g, 30 mmoles, 3 eq.), and potassium iodide (66 mg) were added to a 100 mL round bottom flask and stirred with a magnetic stir bar. The flask was placed in an oil bath at 80° C. and allowed to reflux for 9 hours. The flask was then cooled in an ice bath and the contents was filtered. The filter cake was washed in the filter with a small amount of isopropanol. The filter cake was then slurried 3 times in 20 mL of water and filtered. The resulting slurry was dried to give 3 g of material in 73% yield. The slurry was recrystallized by dissolving in 37 mL of boiling isopropanol, filtered hot and allowed to cool and filtered to give material which had a purity of 99.7% and an overall yield of 60%.

Example 2

Synthesis of Risperidone

The same materials and method as in Example 1 with the exception being that methyl ethyl ketone (MEK) (15 mL) was used instead of 20 mL of isopropanol. The flask was put in an oil bath at 79–83° C. overnight, cooled, filtered and washed with acetone and water to give 2.19 g, 53% yield.

Example 3

Synthesis of Risperidone

The same materials and method as in Example 1 with the exception being that 20 mL of acetonitrile was used instead of 20 mL of isopropanol. The flask was put in an oil bath for 17 hours at 79–83° C., then put in the freezer for 2 hours, filtered, and the filter cake washed with acetone until the filtrate had no color. The filter cake was then slurried in 25 mL water 3 times and filtered and dried to give 3.03 g, 74% yield, of crude risperidone. The crude risperidone was recrystallized from 35 mL of isopropanol, filtered hot, cooled, filtered and dried to give 2.47 g of risperidone, 60% overall yield, 99.8% pure by HPLC.

Example 4

Synthesis of Risperidone

The same materials and method as in Example 1 with the exception being that 20 mL of acetonitrile was used instead of 20 mL of isopropanol. The flask was put in an oil bath for 17 hours at 79–83° C., then put in the freezer for 2 hours, filtered, and the filter cake washed with acetone until the filtrate had no color. The filter cake was then slurried in 25 mL water 3 times and filtered and dried to give 3.03 g, 74% yield, of crude risperidone. The crude risperidone was recrystallized from 75 mL of acetone, filtered hot, cooled, filtered and dried to give 2.25 g of risperidone, 60% overall yield, 99.9% pure by HPLC.

Example 5

Synthesis of Risperidone

The same materials and method as in Example 1 with the exception being that 20 mL of iso-butanol was used instead of 20 mL of isopropanol followed by stirring in an oil bath at 78° C. over night. Risperidone was isolated in 63% yield.

Example 6

Preparation of Risperidone Form B

Risperidone (5.3 g) was dissolved in chloroform (30 mL). Cyclohexane (280 mL) was slowly added to the solution until a cloudy dispersion was formed. The suspension was filtered. The filtrate, analyzed by PXRD, contained risperidone Form B. Further heating overnight at 80° C. under reduced pressure produced risperidone Form A, which was confirmed by PXRD analysis.

Example 7

Preparation of Risperidone Form B

Risperidone (5.0 g) was dissolved in 30 mL chloroform. Hexane (250 mL) was added to the solution until a cloudy dispersion was formed. The suspension was filtered. The isolated filtrate, analyzed by PXRD, contained risperidone Form B. Further heating of the filtrate overnight at 80° C. under reduced pressure produced risperidone Form A, which was confirmed by PXRD analysis.

Example 8

Preparation of Risperidone Form B

Risperidone (5.3 g) was dissolved in 40 ml ethanol. Water (100 mL) was added to the solution until a cloudy dispersion was formed. The resulting suspension was filtered. The isolated filtrate, analyzed by PXRD, contained risperidone Form B. Further heating of the filtrate overnight at 80° C., under reduced pressure, produced risperidone Form A, which was confirmed by PXRD analysis.

Example 9

Preparation of Risperidone Form B

Risperidone (5.0 g) was dissolved in methanol (45 mL). Water (70 ml) was added to the solution until a cloudy dispersion was formed. The suspension was filtered. The isolated filtrate, analyzed by PXRD, contained risperidone Form B. Further heating of the filtrate overnight at 80° C., under reduced pressure, produced risperidone Form A, which was confirmed by PXRD analysis.

Example 10

Preparation of Risperidone Form B in Water

Risperidone (6 g) was dissolved at room temperature in 60 mL of 0.5 N HCl and water (40 mL) was added. The solution was heated in a boiling water bath and stirred with a magnetic stir bar. Concentrated aqueous sodium carbonate was added portion-wise to the solution to facilitate precipitation until a pH of approximately 8 was attained. A precipitate was formed. After cooling to room temperature, the mixture was cooled in an ice bath and filtered to give a mixture of risperidone Form A and risperidone Form B in an 82% yield.

Example 11

Preparation of Risperidone Form A by Crystallization in Organic Solvents

Risperidone (6 g) was added portion-wise and dissolved in a minimum amount of solvent by heating in a boiling water bath (about 95° C.). Suitable solvents and the corresponding suitable volumes are listed below in Table 1. Solvents having a boiling point lower than 95° C. were heated to their boiling point. The solutions were left to cool to room temperature to facilitate precipitation of risperidone Form A. The mixture was then further cooled in an ice bath and then filtered. The precipitate was analyzed by PXRD and found to be risperidone Form A.

TABLE 1

Preparation of Risperidone Form A
The volumes of solvents used per 6 grams of Risperidone

| | |
|---|---|
| DMF: | 40 ml |
| iso-butanol: | 35 ml |
| THF: | 40 ml |
| Acetone: | 200 ml |
| Benzene: | 26 ml |
| methyl ethyl ketone: | 70 ml |
| absolute ethanol: | 35 ml |
| n-butanol: | 45 ml |
| Methanol: | 40 ml |
| Toluene: | 45 ml |
| Acetonitrile: | 100 ml |
| DMSO: | 100 ml |
| ethyl acetate: | 150 ml |
| Isopropanol: | 100 ml |

Example 12

Preparation of Risperidone Form A

Risperidone (5.6 g) was dissolved in 50 mL dichloromethane. Cyclohexane (170 mL) was added to the solution until a cloudy dispersion was formed. The resulting suspension was filtered. The isolated filtrate, analyzed by PXRD, contained risperidone Form A and a minor quantity of risperidone Form B.

Example 13

Preparation of Risperidone Form A

Risperidone (5.1 g) was dissolved in 30 mL dichloromethane. n-Hexane (150 mL) was added to the solution to facilitate precipitation until a cloudy dispersion was formed. The resulting suspension was filtered. The filtrate, analyzed by PXRD, contained risperidone Form A and a minor quantity of risperidone Form B.

Example 14

Preparation of Risperidone Form E

Risperidone (5 g) was dissolved in 60 mL isopropanol. Water (950 mL) was added to the solution to facilitate precipitation until a cloudy dispersion was formed. The suspension was filtered. The filtrate, analyzed by PXRD, contained risperidone Form E.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

What is claimed is:

1. Risperidone Form A which is characterized by x-ray powder diffraction peaks at 14.2±0.2, 21.3±0.2 degrees two-theta.

2. The risperidone Form A of claim 1 which is further characterized by x-ray powder diffraction peaks at 10.6±0.2, 11.4±0.2, 16.4±0.2, 18.9±0.2, 19.9±0.2, 22.5±0.2, 23.3±0.2, 25.4±0.2, 27.6±0.2, 29.0±0.2 degrees two-theta.

3. A risperidone polymorph that is characterized by a powder x-ray diffraction pattern substantially as depicted in FIG. 1.

4. Risperidone Form B which is characterized by x-ray powder diffraction peaks at 14.0±0.2 and 21.7±0.2 degrees two-theta.

5. The risperidone Form B of claim 4 which is further characterized by x-ray powder diffraction peaks at 10.8±0.2, 11.9±0.2, 12.6±0.2, 14.0±0.2, 17.5±0.2, 18.3±0.2, 19.9±0.2, 21.0±0.2, 21.7±0.2 degrees two-theta.

Figure 2:
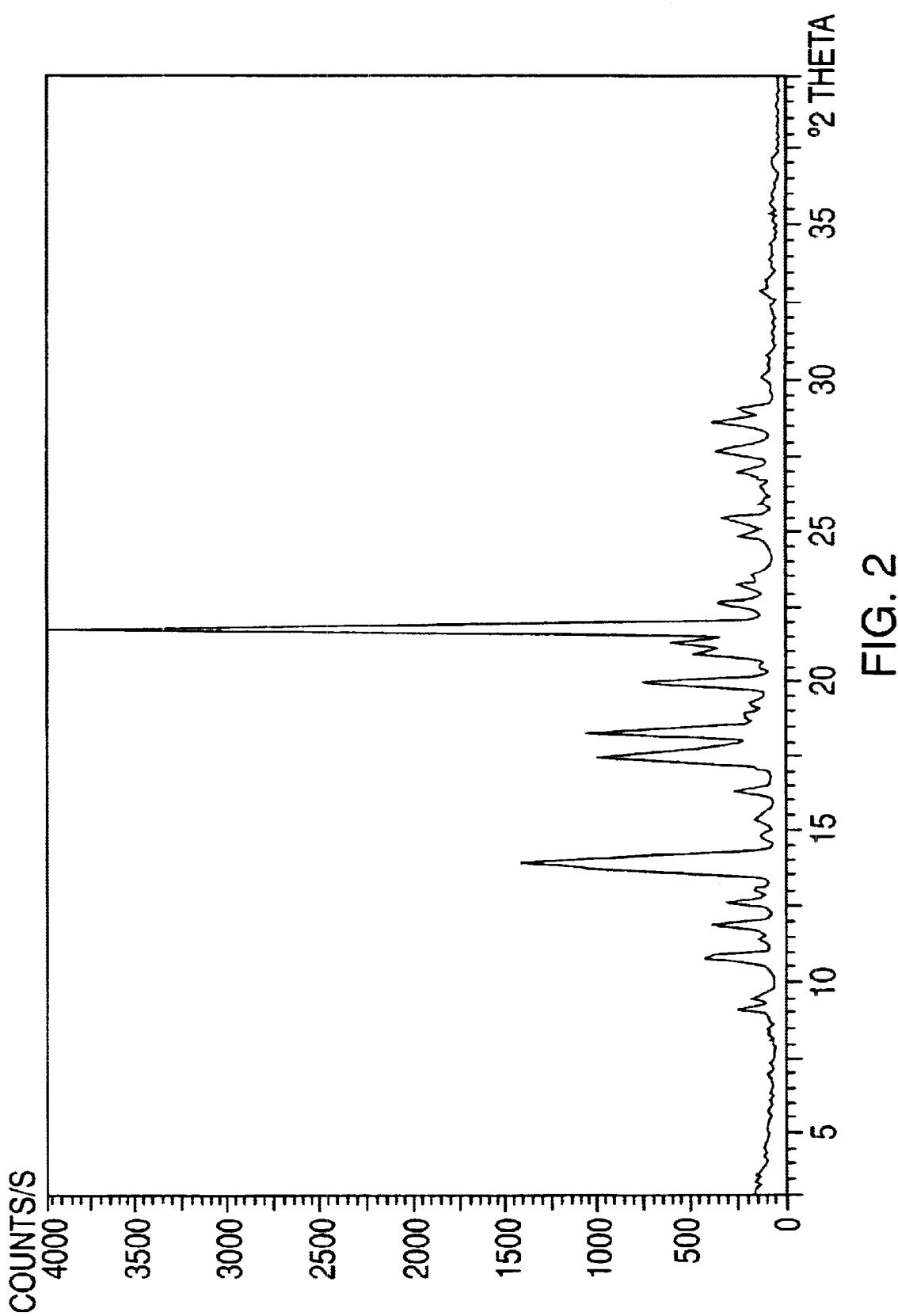
FIG. 2 is a characteristic x-ray powder diffraction spectrum of risperidone Form B.

6. A risperidone polymorph that is characterized by a powder x-ray diffraction pattern substantially as depicted in FIG. 2.

7. Risperidone Form E which is characterized by x-ray powder diffraction peaks at 16.5±0.2, 21.7±0.2 degrees two-theta.

8. The risperidone Form E of claim 7 which is further characterized by x-ray powder diffraction peaks at 16.5±0.2, 12.6±0.2, 21.7±0.2, 15.6±0.2, 17.0±0.2, 18.4±0.2, 19.1±0.2, 21.3±0.2, 24.0±0.2, 24.9±0.2, 27.0±0.2 degrees two-theta.

Figure 3:
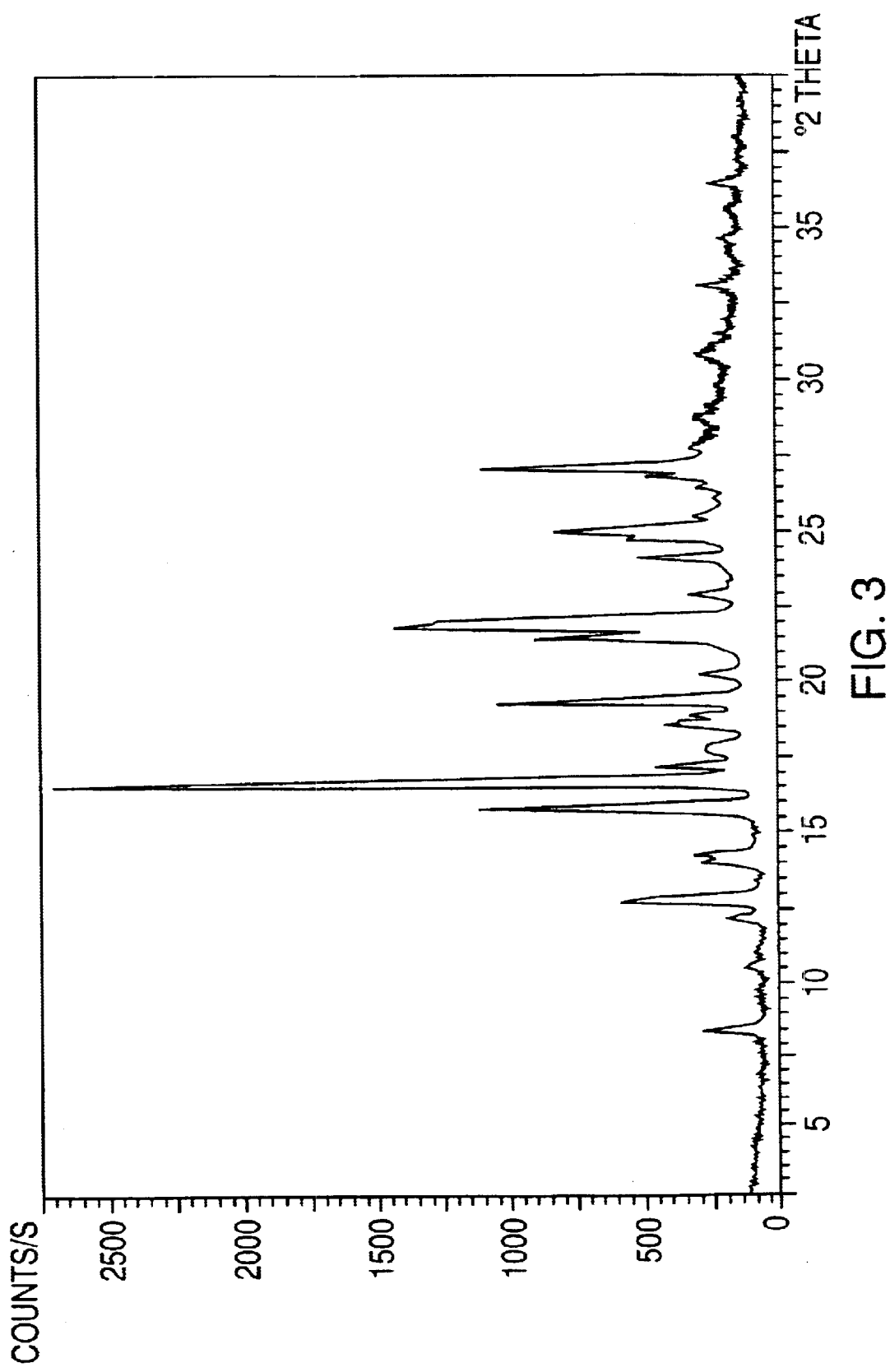
FIG. 3 is a characteristic x-ray powder diffraction spectrum of risperidone Form E.

9. A risperidone polymorph that is characterized by a powder x-ray diffraction to pattern substantially as depicted in FIG. 3.

10. A process for preparing risperidone Form B comprising the steps of:
(a) dissolving risperidone in a water soluble alcohol having 1 to 4 carbon atoms where the ratio of risperidone to alcohol is about 1:7.5 to about 1:9;

(b) adding water to facilitate precipitation; and
(c) isolating risperidone Form B.

11. A process for preparing risperidone Form B comprising the steps of:
   (a) dissolving risperidone in chloroform;
   (b) adding cyclohexane or hexane to facilitate precipitation; and
   (c) isolating risperidone Form B.

12. A process for preparing risperidone Form B comprising the steps of:
   (a) dissolving risperidone in an aqueous solution of HCl;
   (b) adding aqueous $Na_2CO_3$ to facilitate precipitation; and
   (c) isolating risperidone Form B.

13. A process for preparing risperidone Form A comprising the steps of:
   (a) dissolving risperidone in an organic solvent selected from the group consisting of dimethylformamide, tetrahydrofuran, acetone, benzene, ethyl methyl ketone, n-butanol, methanol, isopropanol, absolute ethanol, acetonitrile, toluene, dimethyl sulfoxide, iso-butanol, and ethyl acetate;
   (b) heating the solvent to reflux;
   (c) cooling the solvent to facilitate precipitation; and
   (d) isolating risperidone Form A.

14. A process for preparing risperidone Form A comprising the steps of:
   (a) dissolving risperidone in dichloromethane;
   (b) adding cyclohexane or hexane to facilitate precipitation; and
   (c) isolating risperidone Form A.

15. A process for preparing risperidone Form E comprising the steps of:
   (a) dissolving risperidone in isopropanol where the ratio of risperidone to isopropanol is about 1:12;
   (b) adding water to facilitate precipitation; and
   (c) isolating risperidone Form E.

16. A process for preparing risperidone Form A comprising the steps of:
   (a) heating risperidone Form B at a temperature of about 250° C. to about 800° C. for a time sufficient to induce to formation of risperidone Form A; and
   (b) isolating risperidone Form A.

17. The process of claim 16 wherein the heating takes place under reduced pressure or at atmospheric pressure.

18. The process of claim 16 wherein the temperature is about 800° C.

19. The process of claim 16 wherein the time is about 16 to about 20 hours.

* * * * *

UNITED STATES PATENT AND TRADEMARK OFFICE
CERTIFICATE OF CORRECTION

PATENT NO.   : 6,750,341 B2
DATED        : June 15, 2004
INVENTOR(S)  : Krochmal et al.

It is certified that error appears in the above-identified patent and that said Letters Patent is hereby corrected as shown below:

Column 2,
Line 19, change "can done" to -- can be done --.

Column 6,
Line 48, change "the addition of hexane of cyclohexane" to -- the addition of hexane or cyclohexane --.

Column 10,
Line 61, change "diffraction to pattern" to -- diffraction pattern --.

Column 12,
Line 17, change "250°"" to -- 25° --.
Line 17, change "800°"" to -- 80° --.
Line 24, change "800°"" to -- 80° --.

Signed and Sealed this

Third Day of May, 2005

JON W. DUDAS
*Director of the United States Patent and Trademark Office*